US006833078B2

(12) United States Patent
Espinoza et al.

(10) Patent No.: US 6,833,078 B2
(45) Date of Patent: Dec. 21, 2004

(54) SOLID-LIQUID SEPARATION SYSTEM

(75) Inventors: Rafael L. Espinoza, Ponca City, OK (US); Sergio R. Mohedas, Ponca City, OK (US); Seyi Odueyungbo, Ponca City, OK (US); James Dale Ortego, Ponca City, OK (US)

(73) Assignee: ConocoPhillips Company, Houston, TX (US)

( * ) Notice: Subject to any disclaimer, the term of this patent is extended or adjusted under 35 U.S.C. 154(b) by 203 days.

(21) Appl. No.: 10/243,448

(22) Filed: Sep. 13, 2002

(65) Prior Publication Data
US 2004/0050806 A1 Mar. 18, 2004

(51) Int. Cl.[7] ............................................. B01D 37/00
(52) U.S. Cl. .................... 210/800; 210/806; 210/195.3; 210/251; 210/294; 210/513; 261/3; 208/950; 422/140; 422/147; 518/700; 518/705; 518/709
(58) Field of Search ................................ 210/800, 806, 210/195.3, 194, 251, 294, 513; 261/3, 77; 422/140, 147; 518/700, 705, 709; 208/950

(56) References Cited

U.S. PATENT DOCUMENTS

| 4,605,678 A | 8/1986 | Brennan et al. ............ 518/700 |
| 4,678,860 A | 7/1987 | Kuester ........................ 585/14 |
| 5,407,644 A | 4/1995 | Rytter et al. ................ 422/106 |
| 5,422,375 A | 6/1995 | Rytter et al. ................ 581/700 |
| 5,520,890 A | 5/1996 | Lorentzen et al. .......... 422/197 |
| 5,527,473 A | 6/1996 | Ackerman ................... 210/767 |
| 5,770,629 A | 6/1998 | Degeorge et al. ........... 518/700 |
| 5,811,469 A | 9/1998 | Leviness et al. ............ 518/700 |
| 5,827,903 A | 10/1998 | White et al. ................. 518/710 |
| 5,844,006 A | 12/1998 | Jager et al. ................. 518/700 |
| 5,900,159 A | 5/1999 | Engel et al. ................ 210/788 |
| 5,962,537 A | 10/1999 | Leviness ...................... 518/700 |
| 6,068,760 A | 5/2000 | Benham et al. ............. 208/950 |
| 6,069,179 A | 5/2000 | Rytter et al. ................ 518/700 |
| 6,096,789 A | 8/2000 | Clerici et al. ............... 518/706 |
| 6,217,830 B1 | 4/2001 | Roberts et al. ............. 422/140 |
| 6,344,490 B1 | 2/2002 | DeGeorge et al. .......... 518/700 |
| 2003/0109591 A1 * | 6/2003 | Zhou et al. .................. 518/719 |

FOREIGN PATENT DOCUMENTS

| WO | WO 99/64380 | 12/1999 | ............. C07C/1/07 |
| WO | WO 02/085508 | 10/2002 | |
| WO | WO 02/097007 | 12/2002 | |

OTHER PUBLICATIONS

European Search Report for Appln. No. EP 03 25 5751 dated Feb. 18, 2001 (3 p.).
Bechtel Corporation; *Alternative Fuel and Chemicals From Synthesis gas*; Prepared for Air Products and Chemicals, Inc. Subcontract No. PT5781–B; May 1996; (pp. 1–1 thru Appendix A5–a).
R. L. Espinoza, et al; *Use of Membranes in Fischer–Tropsch Reactors*; Studies in Surface Science and Catalysis 130; 2000 Elsevier Science B.V.; (pp. 389–394).

* cited by examiner

Primary Examiner—Robert A. Hopkins
(74) Attorney, Agent, or Firm—Conley Rose, P.C.

(57) ABSTRACT

Methods and apparatus for separating liquid products and catalyst fines from a slurry used in a Fischer-Tropsch reactor. A settling system continuously or intermittently removes catalyst fines from the slurry and is coupled with catalyst-liquid separation system that separates liquid products from the slurry. The preferred separation system produces a sub-particle rich stream and a catalyst-lean stream that are removed from the system. The systems of the present invention act to reduce the concentration of catalyst fines in the reactor, thereby increasing the effectiveness of a catalyst-liquid separation system.

31 Claims, 4 Drawing Sheets

SOLID-LIQUID SEPARATION SYSTEM

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates generally to methods and apparatus for separating liquid products from a slurry comprising solid particles and liquids. More specifically, the present invention relates to methods and apparatus for separating liquid products from a slurry used in a Fischer-Tropsch slurry bubble column reactor.

A Fischer-Tropsch reaction generally entails contacting a stream of synthesis gas (hydrogen and carbon monoxide) with a catalyst under temperature and pressure conditions that allow the synthesis gas to react and form hydrocarbons. More specifically, the Fischer-Tropsch reaction is the catalytic hydrogenation of carbon monoxide to produce any of a variety of products ranging from methane to higher alkanes, olefins, and oxygenated hydrocarbons or oxygenates. Research continues on the development of more efficient Fischer-Tropsch catalyst systems and reaction systems that increase the selectivity for high-value hydrocarbons in the Fischer-Tropsch product stream.

Originally, the Fischer-Tropsch synthesis was operated in fixed bed reactors. These reactors have several drawbacks, such as temperature control, that can be overcome by gas-agitated slurry reactors or slurry bubble column reactors. Gas-agitated reactors, sometimes called "slurry reactors" or "slurry bubble columns," operate by suspending catalytic particles in liquid and feeding gas reactants into the bottom of the reactor through a gas distributor, which produces small gas bubbles. As the gas bubbles rise through the reactor, the reactants are absorbed into the liquid and diffuse to the catalyst where, depending on the catalyst system, they are converted to gaseous and liquid products. As gaseous products are formed, they enter the gas bubbles and are collected at the top of the reactor.

Because of the formation of liquid products (commonly called waxes in this context), it is necessary to maintain the slurry at a constant level by continuously or intermittently removing liquid products from the reactor. One problem with the removal of liquids, however, is that catalyst particles are dispersed in the liquid and must be separated from the slurry and, in some cases, returned to the reactor in order to maintain a constant inventory of catalyst in the reactor. Several means have been proposed for separating the catalyst from the liquid products, e.g., centrifuges, sintered metal filters, cross-flow filters, magnetic separators, gravitational settling, etc.

Filtration is one of the catalyst-liquid separation methods used with Fischer-Tropsch reactors. Filtration techniques are characterized by solid-liquid separation systems that remove liquid products from a slurry by drawing the fluid across a filter medium. The filter medium may be simply a filter substrate or may be composed of a filter cake disposed on a filter substrate, such that the filter cake forms a primary filter. A filter cake is formed as solid particles are deposited on the filter substrate creating a permeable barrier between the slurry and the substrate. The thickness and permeability of the filter cake is critical to the efficient operation of the filtration system.

In a commercial slurry bubble column reactor, the severe hydrodynamic conditions inside the reactor, coupled with the desired long lifetime of the catalytic material, typically results in catalyst attrition. As the catalyst breaks down over time, sub-particles of various sizes may be created, including very small particles known as "fines," some of which may even be sub-micron in size. The presence of fines in the reactor tends to greatly reduce the effectiveness of the catalyst-liquid separation system.

In a catalyst-liquid separation system utilizing filtration, cycle time between backwashing operations, as well as filter life, may be greatly reduced because the fines tend to reduce the permeability and flux of the filter system. Likewise, centrifuges and gravitational settlers have been found unsuccessful in reducing the percentage of fines because the fine particles are so small that they will not settle out of the liquid solution in a practical amount of time, if at all. Magnetic separation has been similarly ineffective in removing catalyst fines from the slurry. Thus the performance of a catalyst-liquid separation system has hereto been undesirably dependent upon the age of the catalyst. For example, when the catalyst is new the catalyst-liquid separation system operates at a very high rate that decreases as the catalyst breaks down.

Thus, there remains a need in the art for methods and apparatus to maintain the effectiveness of a catalyst-liquid separation system independent of the age or degree of attrition of the catalyst. Therefore, the embodiments of the present invention are directed to methods and apparatus for removing catalyst fines from a slurry that seek to overcome the limitations of the prior art.

SUMMARY OF THE PREFERRED EMBODIMENTS

Accordingly, there are provided herein methods and apparatus for separating liquid products and catalyst fines from a slurry used in a Fischer-Tropsch reactor. The preferred embodiments of the present invention are characterized by a settling system that continuously or intermittently removes catalyst sub-particles fines from the slurry by way of a sub-particle rich stream, coupled with a distinct separation system that separates the slurry into a catalyst-rich stream and a catalyst-lean stream that supplies most of the commercial products of the reactor system. The embodiments of the present invention act to reduce the overall concentration of catalyst fines in the slurry, thereby increasing the effectiveness and/or the life of a catalyst-liquid separation system.

One preferred embodiment includes a slurry bubble column reactor system having a first circulation loop with a catalyst-liquid separation system that separates the slurry into a catalyst-rich stream and a catalyst-lean stream. The catalyst-lean stream provides a stream from which most of the products of the reactor can be extracted. In this embodiment, the reactor system also includes a second circulation loop that, in some preferred embodiments, comprises a settling chamber, which segregates at least a portion of catalyst sub-particles from catalyst particles. A sub-particle lean stream and a sub-particle rich stream can then be extracted from the settling chamber. The sub-particle rich stream, which may contain a portion of the liquid products, can then be removed from the system, and may be further processed if desired to recover some of the liquid products. It will be understood that the terms "rich" and "lean" are relative terms, so that, for example, "sub-particle rich stream" refers to a stream containing a higher proportion of sub-particles, as compared to other particles, than other streams in the system. The overall concentration of catalyst fines in the slurry is maintained at a reduced level, thereby increasing the effectiveness and life of the catalyst-liquid separation system.

In a second preferred embodiment, a slurry bubble column reactor system has only one circulation loop, which includes both a settling chamber and a catalyst-liquid separation system. The slurry moves through the settling chamber, from which is extracted a sub-particle rich stream that is removed from the system. The sub-particle lean stream can then be processed in the catalyst-wax separation system to produce a catalyst-rich stream and a catalyst-lean stream. Production quantities of liquid products can then be collected from the catalyst-lean stream. In addition, some liquid products can be recovered from the sub-particle rich stream after further processing.

The present invention may also be embodied as a method for removing solids from a slurry by circulating the slurry through a settling chamber to produce a sub-particle lean stream and circulating the slurry through a catalyst-liquid separation system to produce a catalyst-lean stream. The preferred embodiment may also include removing the sub-particle lean stream and the catalyst-lean stream from the system.

Thus, the present invention comprises a combination of features and advantages that enable it to substantially reduce the concentration of catalyst fines in the slurry, thereby increasing filter effectiveness and life. These and various other characteristics and advantages of the present invention will be readily apparent to those skilled in the art upon reading the following detailed description of the preferred embodiments of the invention and by referring to the accompanying drawings.

BRIEF DESCRIPTION OF THE DRAWINGS

For a more detailed understanding of the preferred embodiments, reference is made to the accompanying Figures, wherein.

DETAILED DESCRIPTION OF THE PREFERRED EMBODIMENTS

Figure 1:
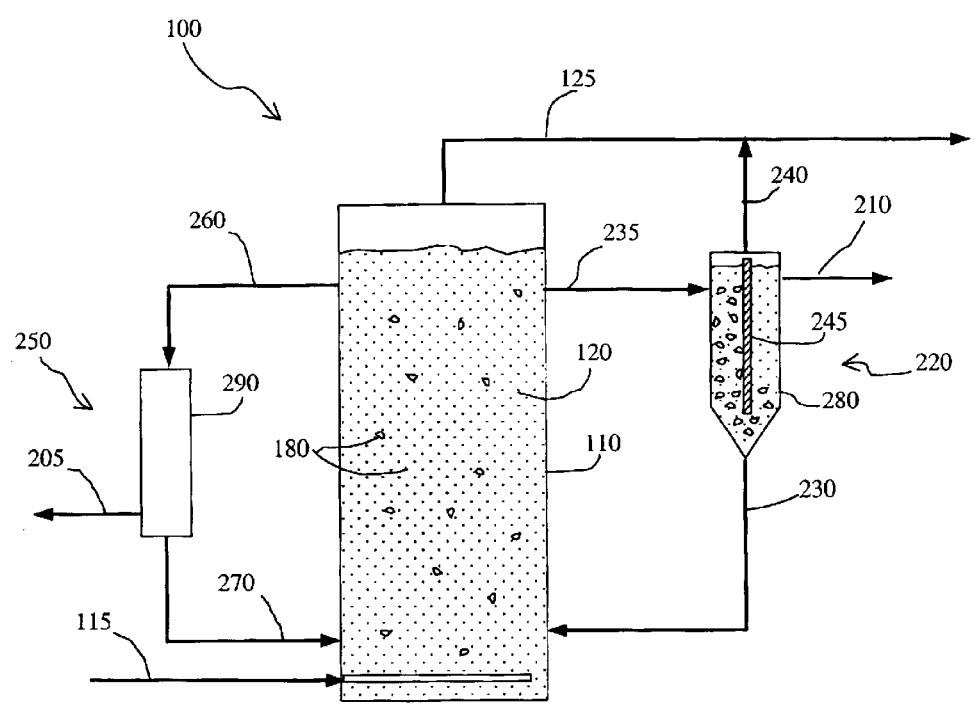
FIG. 1 is one embodiment of a slurry bubble column reactor system having two circulation loops.

In the description that follows, like parts are marked throughout the specification and drawings with the same reference numerals, respectively. The figures are not necessarily to scale. Certain features of the invention may be shown exaggerated in scale or in somewhat schematic form and some details of conventional elements may not be shown in the interest of clarity and conciseness.

The preferred embodiments of the present invention relate to methods and apparatus for effectively removing liquid products from a slurry containing solid catalyst particles, at least a portion of which are very small catalyst sub-particles, or fines, formed by catalyst attrition. The present invention is susceptible to embodiments of different forms. There are shown in the drawings, and herein will be described in detail, specific embodiments of the present invention with the understanding that the present disclosure is to be considered an exemplification of the principles of the invention, and is not intended to limit the invention to that illustrated and described herein.

In particular, various embodiments of the present invention provide a number of different methods and apparatus for removing liquid products from a slurry. The concepts of the invention are discussed in the context of a Fischer-Tropsch slurry bubble column reactor but, use of the concepts of the present invention is not limited to slurry bubble column reactors or to the Fischer-Tropsch process in general and may find use in any reacting or non-reacting fluid-solid system, or any filtering or separating application. It is to be fully recognized that the different teachings of the embodiments discussed below may be employed separately or in any suitable combination to produce the desired results. In the context of the current description, the slurry is defined as a liquid that contains solid particles of any concentration. The slurry should not be read as indicating a specific concentration of solid particles within the fluid. It should also be understood that the concentration of solid particles within the slurry will change, depending on the location of the slurry within the reactor assembly.

As used herein, reactor slurry is defined as the composition of catalyst particles and hydrocarbon liquids generally found in the reactor. It is understood that the exact composition of the reactor slurry within the reactor may not be constant throughout the reactor and that the exact composition of the reactor slurry is not critical to the operation of the separation techniques discussed herein.

In the current context, the sub-particle rich stream is defined as a stream of slurry that has had a portion of the larger catalyst particles removed. Therefore, among the catalyst in the sub-particle rich stream, there is a higher concentration of catalyst sub-particles as compared to the composition of catalyst in the reactor slurry. A sub-particle lean stream is defined as a stream of slurry from which some catalyst sub-particles have been removed. Therefore, among the catalyst in the sub-particle lean stream, there is a lower concentration of catalyst sub-particles as compared to the composition of catalyst in the reactor slurry.

A catalyst-lean stream is defined as a stream of slurry from which the majority of the catalyst particles have been removed. The catalyst-lean stream has a lower concentration of catalyst particles than the reactor slurry and is preferably substantially free of catalyst particles in order to be suitable for further processing into commercial products. A catalyst-rich stream is defined as a stream of slurry from which a portion of the liquid hydrocarbons has been removed. The catalyst-rich stream therefore has a higher concentration of catalyst particles than the reactor slurry.

Referring now to FIG. 1, a slurry bubble column reactor system 100 includes a slurry reactor 110, a settling system 220, and a catalyst-liquid separation system 250. Reactor 110 includes a reactor chamber 120 containing a catalyst 180 suspended in a slurry. Settling system 220 includes settling chamber 280, lines 230 and 235 connecting the settling chamber to reactor 110, sub-particle rich stream outlet 210, and gas outlet 240. Optionally, a degasser vessel (not shown) may remove gas from the slurry before it enters chamber 280. Settling system 220 may also include an internal plate 245, or other internal structure, for improving the settling characteristics of chamber 280. Catalyst-liquid separation system 250 includes a separation unit 290 connected to reactor 110 by lines 260 and 270. Separation system 250 also includes outlet 205 for the catalyst-lean stream to provide substantially solids-free hydrocarbon products. Optionally, a degasser vessel (not shown) may remove gas from the slurry before it enters separation unit 290.

A feed gas is supplied through line 115 into reactor 110 that is filled with a reactor slurry. Product gases flow through gas outlet 125 while liquid products combine with the reactor slurry. Reactor slurry passes into settling system 220 via line 235 and into catalyst-liquid separation system 250 via line 260. Catalyst-liquid separation system 250 produces a catalyst-lean stream through outlet line 205 and recycles a catalyst-rich stream to reactor 110 through line 270. Settling system 220 produces a sub-particle rich stream through outlet 210 and a sub-particle lean stream, which is recycled to reactor 110 through line 230. A preferred settling system 220 also provides an outlet for gas through outlet 240. Gas outlet 125 from reactor 110 and gas outlet 240 from settling system 220 can be combined into one single gas outlet, as shown in FIG. 1, but it should be understood that they do not necessarily need to be combined. It is also understood that any gas outlet from any optional degasser (not shown) also could be combined or not with any of the two gas outlets 125 and 240. Settling system 220 and catalyst-liquid separation system 250 create two distinct flow loops that circulate slurry.

Slurry bubble column reactors, such as reactor 110 shown in FIG. 1, function by bubbling gas through inlet 115 into a reactor slurry in which are suspended particles comprising a catalyst 180. As the gas bubbles rise through the reactor, the reactants are absorbed into the reactor slurry and diffuse to the catalyst where, depending on the catalyst system, they are converted to gaseous and liquid products. Gas products exit the top of reactor 110 through gas outlet line 125 while liquid products mix with the reactor slurry. One exemplary slurry bubble column reactor is described in co-owned U.S. patent application Ser. No. 10/023,258, titled "Slurry Bed Reactor With Well-Mixed Gas Flow Regime," which is incorporated herein by reference for all purposes.

Figure 2:
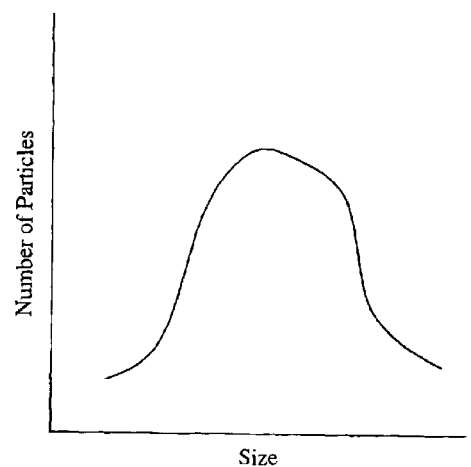
FIG. 2 is a graph depicting the size distribution of an unused catalyst system.
Figure 3:
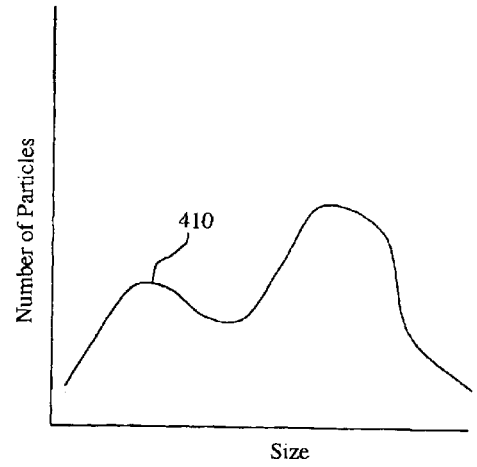
FIG. 3 is a graph depicting the size distribution of a used catalyst system.

Therefore, the liquid products must continuously be removed from the reactor slurry in order to maintain the total volume of liquids contained in the reactor. The effectiveness of the catalyst-liquid separation may also be dependent on the size of the catalyst particles found in the circulating slurry. In a given reactor slurry, catalyst particles ranging in diameter from less than 1 micron to as much as tens of microns may be present. FIG. 2 shows a model size distribution for a newly fabricated catalyst. As the reactor operates, the catalyst particles are subjected to extreme hydrodynamic conditions that will, over time, tend to break down the catalyst into increasingly smaller particles. As shown in FIG. 3, after being used for a period of time, the distribution of particle size will change to include an increasing number of very small particles, as indicated at 410. It is these very small catalyst sub-particles (fines) that not only decrease the effectiveness of the catalyst-liquid separation system but may have other detrimental effects on the system as a whole.

Figure 4:
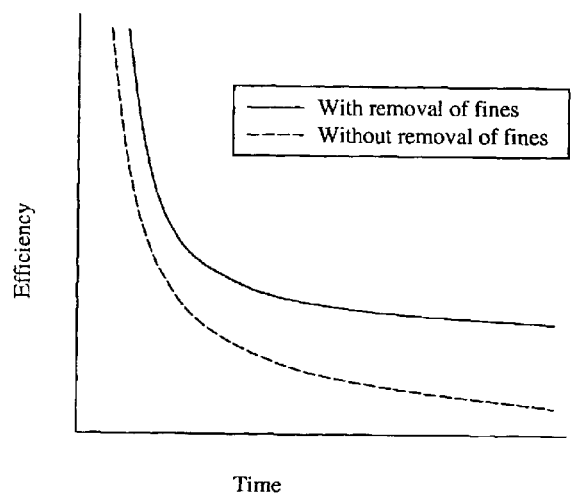
FIG. 4 is a graph illustrating the expected performance curves of a filter operating with and without removal of fines.

As previously discussed, the liquid products produced by the reaction are separated from the reactor slurry in a catalyst-liquid separation unit. One of the preferred types of separation units uses filtration to separate the solid catalyst particles from the liquid products. Although filtration has proven to be very effective in providing a clean liquid product, filters are also susceptible to a loss of permeability or flux, especially in the presence of a high concentration of solids, in particular catalyst fines. The dashed line of FIG. 4 illustrates the filtration effectiveness of a typical filter element over a period of time. It can be seen that the effectiveness of a typical filter element decreases with time until it becomes necessary to clean or replace the filter element.

Referring back to FIG. 1, in order to control the accumulation of catalyst fines in the reactor slurry, reactor system 100 includes separation system 220. Reactor slurry enters settling chamber 280 from reactor 110 via line 235. Settling chamber 280 is arranged so that the reactor slurry will move through chamber 280 with a velocity such that solid catalyst particles having at least a predetermined size will settle towards the bottom of the chamber and be recycled into reactor chamber 120 via line 230. Particles smaller than the predetermined size will remain suspended. Outlet line 210 is provided to draw off a sub-particle rich stream and is specifically sized, placed, and operated so as to remove a minimum amount of catalyst particles having at least the predetermined size. Therefore, the sub-particle rich stream that is drawn off through outlet 210 will preferably only contain those catalyst sub-particles (fines) that are detrimental to the system. The flow rate of the sub-particle rich stream through outlet 210 and the slurry level in the settling chamber 280 can each be controlled so as to continuously or intermittently remove catalyst fines from the reactor slurry, thereby reducing or maintaining the overall quantity of catalyst fines in the reactor system. The sub-particle rich stream through outlet 210 can be further processed continuously or intermittently to recover liquid products.

Thus, the presence of catalyst fines in the reactor slurry can be controlled by using settling system 220 to continuously or intermittently remove the undesirable particles from the system. The particle size distribution within the reactor slurry can then be maintained within a desired range in order to improve the effectiveness of the catalyst-liquid separation, in particular filtration. Because the present system prevents the catalyst particle size distribution from deteriorating significantly over time, the catalyst-liquid separation system does not have to be designed to accommodate the eventual accumulation of catalyst fines. This enables the use of more effective filtration systems. FIG. 4 illustrates the improvement in filter efficiency wherein the dotted line illustrates the efficiency of a typical filtration system over time and the solid line corresponds to an improved efficiency of a filtration system constructed in accordance with the preferred embodiments, in which most of the catalyst fines are selectively removed from the system.

Settling system 220 helps to remove catalyst fines by taking advantage of the density difference between the solid catalyst and the liquid hydrocarbons. Settling system 220 is preferably a gravitational sedimentation system but may also be a centrifuge, a hydrocyclone, or some other device that seeks to take advantage of the density differences between the catalyst and the hydrocarbons. The settling of single particles can be described using a combination of Newton's law, which relates to the forces acting on the particle, and Stokes' law, which takes into account the drag forces on the particle as it moves through the fluid. The time (t) that it takes for a particle to travel a distance (L) is given by:

$$t = (18/G)(\mu/\rho)(L/D^2) \qquad (1)$$

where t is the fall time (sec), ρ is the particle density (g/cm$^3$), μ is the viscosity of the liquid (g/cm-sec), L is the fall distance (cm), D is the particle diameter (cm), and G is the effective acceleration (cm/sec$^2$) given by:

$$G = g\left(1 - \frac{\rho_f}{\rho}\right)N \qquad (2)$$

where g is the acceleration due to gravity (980 cm/sec$^2$), $\rho_f$ is the fluid density (g/cm$^3$), and N is the number of g's.

As can be seen in Equation 1, the time (t) that it takes for a particle to settle a given distance is dependent on its diameter. The larger the diameter of the particle, the faster the particle will settle. Therefore, the difference in settling velocity of particles with different diameters can be used to segregate the particles according to their size.

Figure 5:
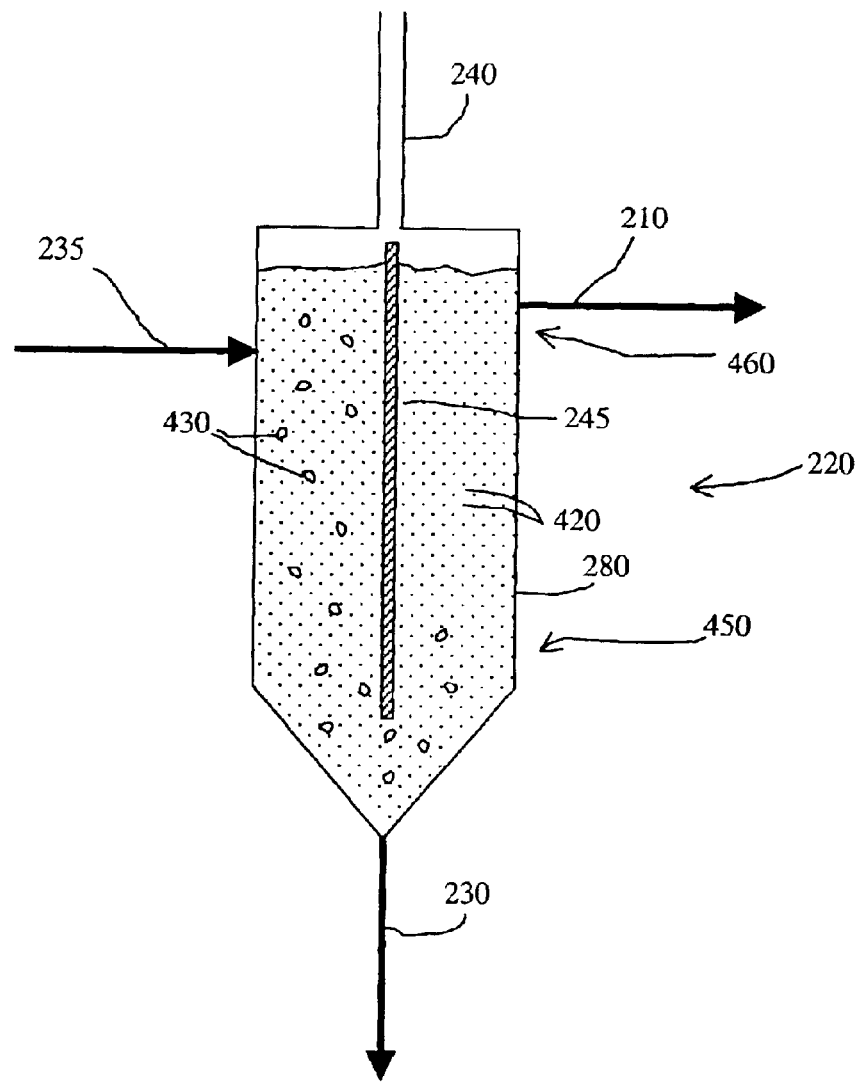
FIG. 5 is a detailed view of one embodiment of a preferred settling system.

Referring now to FIG. 5, one embodiment of settling system 220 is shown. Settling system 220 includes a settling chamber 280 that has inlet line 235 and outlet lines 210, 230, and 240. Suspended in the reactor slurry as it enters settling chamber 280 are catalyst particles 430 and catalyst sub-particles 420. Settling chamber 280 is sized so as to control the velocity of the reactor slurry as it moves through the chamber. The flow through outlet 210 is preferably controlled so as to encourage sedimentation of catalyst particles.

As the reactor slurry enters chamber 280, catalyst particles 420 and 430 will move towards lower portion 450 of the chamber at different settling velocities. As shown by Equation 1, particles 430 will have a higher settling velocity than sub-particles 420. Outlet 210 is preferably located near upper portion 460 of chamber 280 and draws a sub-particle rich stream from the chamber Outlet 210 preferably draws the sub-particle rich stream with a controlled flow so that the overflow velocity of the liquids is lower than the settling velocity of particles 430 but higher than the settling velocity of sub-particles 420.

Therefore, chamber 280 and outlet 210 can be designed so that primarily the catalyst fines having a certain size are removed through the outlet via the sub-particle rich stream. Outlet 210 may actually comprise several individual outlets as may be required to meet the separation requirements of the reactor. A plate, or other vessel internal structure, may be used to improve the performance of settler 220. A portion of the liquid products can therefore be recovered via line 210 after further processing to remove the fines 420.

Referring back to FIG. 1, for the purpose of discussion only, and by way of an example, the operation of reactor system 100 will be described as a Fischer-Tropsch reactor system. Syngas, containing hydrogen and carbon monoxide, is fed through inlet line 115 into reactor chamber 120, which contains catalyst particles 180 suspended in a slurry. As the syngas bubbles travel through the reactor slurry, the reactants (hydrogen and carbon monoxide) are absorbed into the liquid hydrocarbons present in the slurry and diffuse to the catalyst where they are converted to gaseous and liquid products. The gas products are removed from reactor 120 through line 125 while liquid products mix with the reactor slurry.

Figure 6:
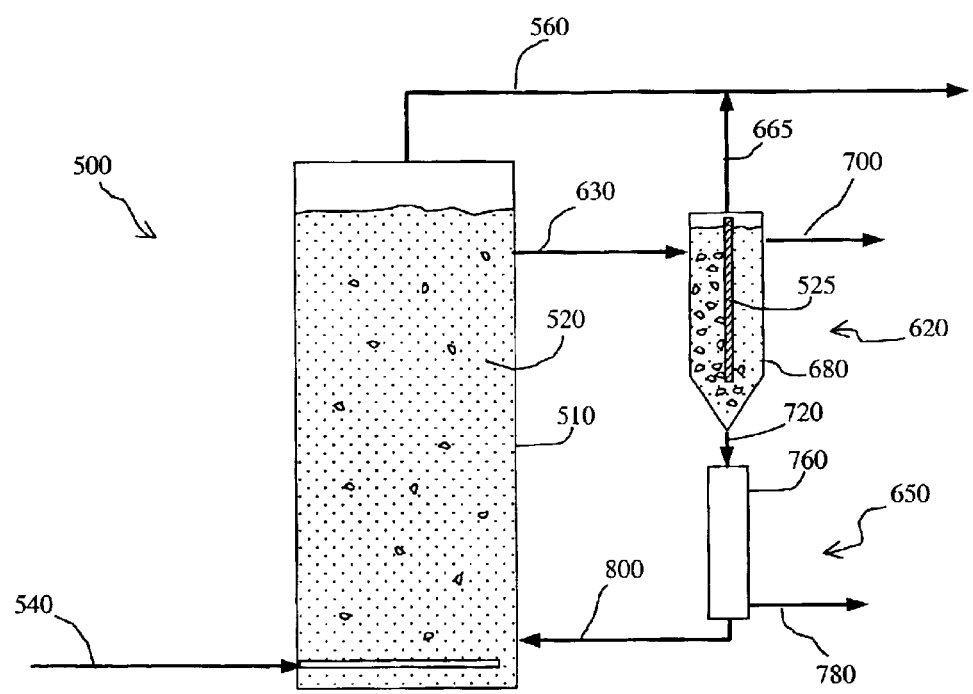
FIG. 6 is one embodiment of a slurry bubble column reactor having a single circulation loop.

Preferably located near the top of the reactor chamber 120, lines 235 and 260 draw off reactor slurry from the reactor into settling system 220 and catalyst-liquid separation system 250, respectively. Settling and separation systems 220 and 250 may be gravity fed and rely on the density difference between the slurry inside the reactor, which is mixed with gas, and the slurry outside the reactor, which is substantially gas-free. Although systems 220 and 250 are depicted as forming separate, distinct flow loops through which the slurry is circulated, they may also operate on a single flow loop, as shown in FIG. 6 and discussed in detail below. It should be understood that more than one settling system 220 and/or more than one catalyst-liquid separation system 250, either arranged in series, parallel or suitable combinations, may be used.

Referring again to FIG. 1, in settling system 220, slurry enters settling chamber 280 through line 235. Outlet 210 acts, as described above, to draw off a sub-particle rich stream while minimizing the loss of catalyst particles above a predetermined size. The remaining sub-particle lean stream, which contains particles of catalyst 180 having at least a predetermined size, exits chamber 280 and is recycled into reactor 110 via line 230. The sub-particle rich stream that is withdrawn through outlet 210 is preferably further processed to separate the sub-particle from the liquid products. Settling system 220 may operate continuously or intermittently as required to maintain the accumulation of catalyst fines in the slurry within desired limits.

In catalyst-liquid separation system 250, reactor slurry enters separation unit 290 via line 260. Separation unit 290 removes catalyst 180 from the slurry and produces a catalyst-lean stream through outlet 205. A catalyst-rich stream is recycled to reactor 110 via line 270 while the output of the catalyst-lean stream through outlet 205 provides most of the products that are liquid at operating temperature and pressure of reactor system 100. Separation unit 290 may use filtration, gravitational separation, magnetic separation, or any other method to produce a relatively clean liquid product. One such filtration system is discussed in Provisional Patent Application No. 60/372,961, titled "Solid/Liquid Separation System for Multiphase Converters," which is hereby incorporated by reference herein for all purposes.

Referring now to FIG. 6, an alternative embodiment of a slurry bubble column reactor system 500 is shown. Reactor system 500 includes reactor 510 and a single circulation loop that includes both a settling system 620 and a catalyst-liquid separation system 650. As in FIG. 1, reactor 510 includes a reactor chamber 520 containing a catalyst suspended in a slurry. Gas inlet line 540 provides feed gas to reactor 510 while gas outlet 560 removes gases from the reactor. Settling system 620 includes line 630 providing reactor slurry from reactor 510 to settling chamber 680. Settling system 620 also includes a first outlet 700 for a sub-particle rich stream that removes material from system 500, a gas outlet 665, and a second outlet line 720. Optionally, a degasser vessel (not shown) may remove gas from the slurry before it enters chamber 680. Gas outlet 560 from reactor 510 and gas outlet 665 from settling system 620 can be combined into one single gas outlet, as shown in FIG. 6, but it should be understood that they do not necessarily need to be combined. It is also understood that any gas outlet from any optional degasser also could be combined or not with any of the two gas outlets 560 and 665.

Catalyst-liquid separation system 650 draws reactor slurry from outlet line 720 into separation unit 760, which outputs a catalyst-lean stream through a first outlet 780 and recycles a catalyst-rich stream into reactor chamber 520 through second outlet line 800. Alternatively, the location of catalyst-liquid separation system 650 and settling system 620 can be reversed such that settling system 620 is downstream of catalyst-liquid separation system 650. Settling system 620 may also optionally include an internal plate 525, or other internal structure, for improving the settlement characteristics of chamber 680.

Although the removal of catalyst fines from the slurry provides desirable benefits to catalyst-liquid separation that uses filtration, other catalyst-liquid separation mechanisms may also be aided by the control of fines, increasing the overall efficiency of the liquid-solids separation system. Some of the other separation techniques that will benefit are magnetic-based techniques, gravitational-based techniques, such as centrifugation, settling, or hydrocyclone solubility-based techniques, and coagulation.

The embodiments set forth herein are merely illustrative and do not limit the scope of the invention or the details therein. It will be appreciated that many other modifications and improvements to the disclosure herein may be made without departing from the scope of the invention or the inventive concepts herein disclosed. Because many varying and different embodiments may be made within the scope of the present inventive concept, including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed is:

1. A slurry bubble column reactor system comprising:
   a reactor containing solid catalyst particles and liquid products suspended in a slurry;
   a first separation unit adapted to produce a sub-particle rich stream comprising at least a portion of the catalyst particles having a size below a predetermined limit from the slurry; and
   a second separation unit adapted to produce a catalyst-lean stream comprising at least a portion of the liquid products from the slurry,
   wherein the sub-particle rich stream and the catalyst-lean stream are removed from the reactor system.

2. The system of claim 1 wherein said first separation unit is adapted to produce a sub-particle lean stream that is recycled into said reactor.

3. The system of claim 1 wherein said first separation unit is adapted to produce a sub-particle lean stream that feeds said second separation unit.

4. The system of claim 1 wherein said second separation unit is adapted to produce a catalyst-rich stream that is recycled into said reactor.

5. The system of claim 1 wherein said second separation unit is adapted to produce a catalyst-rich stream that feeds the first separation system.

6. The system of claim 1 wherein said first separation unit comprises a settling system.

7. The system of claim 6 wherein the settling system utilizes gravitational settling.

8. The system of claim 1 wherein the second separation unit comprises a catalyst-liquid separation system.

9. The system of claim 8 wherein the catalyst-liquid separation system comprises a filtration system.

10. The system of claim 1 wherein the sub-particle rich stream further comprises at least a portion of the liquid product.

11. A slurry bubble column reactor system comprising:
    a reactor containing solid catalyst particles, including sub-particles, and liquid products suspended in a slurry;
    a first flow loop comprising a first separation unit that removes a sub-particle rich stream from the system; and
    a second flow loop comprising a second separation unit that removes a catalyst-lean stream from the system.

12. The system of claim 11 wherein said first separation unit comprises a settling system that utilizes gravitational forces to produce the sub-particle rich stream.

13. The system of claim 11 wherein said sub-particle rich stream further comprises at least a portion of the liquid products, further including means for recovering liquid products from said sub-particle rich stream.

14. The system of claim 11 wherein said second separation unit comprises a catalyst-liquid separation system adapted to produce the catalyst-lean stream.

15. The system of claim 14 wherein said catalyst-liquid separation system comprises a filtration system.

16. A slurry bubble column reactor system comprising:
    a reactor containing solid catalyst particles and liquid products suspended in a slurry, wherein the solid catalyst particles include sub-particles;
    a first outlet in said reactor directing a portion of the slurry from the reactor to a first separation unit, wherein the first separation unit removes a sub-particle rich stream from the system; and
    a second outlet in said reactor directing a portion of the slurry from the reactor to a second separation device, wherein the second separation unit removes a catalyst-lean stream from the system.

17. The system of claim 16 further comprising a first flow loop connected to said first outlet.

18. The system of claim 16 wherein said first separation unit comprises a settling system that utilizes gravitational forces to remove the sub-particle rich stream.

19. The system of claim 16 further comprising a second flow loop connected to said second outlet.

20. The system of claim 16 wherein said second separation unit comprises a catalyst-liquid separation system adapted to produce the catalyst-lean stream.

21. The system of claim 20 wherein said catalyst-liquid separation system comprises a filtration system.

22. The system of claim 16 wherein said sub-particle rich stream includes at least a portion of the liquid products.

23. A method for separating catalyst particles from liquid products in a slurry in a reactor, comprising:
    removing a portion of the slurry from the reactor and passing the slurry through a first separation unit such that the first separation unit removes a sub-particle rich stream; and
    removing a portion of the slurry from the reactor and passing the slurry through a second separation unit such that the second separation unit removes a catalyst-lean stream.

24. The method of claim 23 wherein the sub-particle rich stream is removed in a first flow loop comprising the first separation unit, wherein said first separation unit is a settling system that utilizes gravitational forces.

25. The method of claim 23 wherein the catalyst-lean stream is removed in a second flow loop comprising the second separation unit, wherein said second separation unit is a catalyst-liquid separation system.

26. The method of claim 25 wherein said catalyst-liquid separation system comprises a filtration system.

27. The method of claim 23 wherein said sub-particle rich stream comprises at least a portion of the liquid products, further including means for recovering liquid products from said sub-particle rich stream.

28. A slurry bubble column reactor comprising:
    solid catalyst particles and liquid products suspended in a slurry;
    a first separation device that divides at least a portion of the slurry into a sub-particle rich stream and a sub-particle lean stream;
    a first outlet from said first separation device that removes the sub-particle rich stream from the reactor; and a second separation device adapted to divide the sub-particle lean stream into a catalyst-rich stream and a catalyst-lean stream.

29. The reactor of claim 28 wherein said first separation device further comprises a settling system that utilizes gravitational forces to divide the slurry.

30. The reactor of claim 28 wherein said second separation device comprises a filtration system.

31. The reactor of claim 28 wherein said sub-particle rich stream includes at least a portion of the liquid products.

* * * * *